(12) United States Patent
Walheim et al.

(10) Patent No.: US 8,780,351 B2
(45) Date of Patent: Jul. 15, 2014

(54) METHOD FOR DEMONSTRATING THE PRESENCE OF MOLECULES BY MEANS OF OPTICAL GRATINGS

(75) Inventors: Stefan Walheim, Weingarten (DE); Thomas Schimmel, Karlsruhe (DE); Steven Lenhert, Tallahassee, FL (US); Harald Fuchs, Nottuln (DE); Falko Brinkmann, Hamburg (DE); Thomas Laue, Eggenstein-Leopoldshafen (DE)

(73) Assignee: Karlsruher Institut fuer Technologie, Karlsruhe (DE)

( * ) Notice: Subject to any disclaimer, the term of this patent is extended or adjusted under 35 U.S.C. 154(b) by 448 days.

(21) Appl. No.: 13/319,269

(22) PCT Filed: Apr. 24, 2010

(86) PCT No.: PCT/EP2010/002534
§ 371 (c)(1),
(2), (4) Date: Feb. 21, 2012

(87) PCT Pub. No.: WO2010/127780
PCT Pub. Date: Nov. 11, 2010

(65) Prior Publication Data
US 2012/0154817 A1       Jun. 21, 2012

(30) Foreign Application Priority Data

May 5, 2009    (DE) .......................... 10 2009 019 717

(51) Int. Cl.
*G01N 21/00*     (2006.01)
*G01N 21/55*     (2014.01)

(52) U.S. Cl.
USPC ........................................ 356/432; 356/445

(58) Field of Classification Search
USPC ................... 356/445–448, 450–458
See application file for complete search history.

(56) References Cited

U.S. PATENT DOCUMENTS 5,633,724 A * 5/1997 King et al. ..................... 356/445
6,731,388 B1 * 5/2004 Simon et al. .................. 356/445
(Continued)

FOREIGN PATENT DOCUMENTS

WO    WO-00/41213       7/2000
WO    WO-2008/156732    12/2008

OTHER PUBLICATIONS

International Search Report of PCT/EP2010/002534 Filed Jul. 5, 2010 along with an English Translation.

(Continued)

*Primary Examiner* — Gregory J Toatley
*Assistant Examiner* — Jarreas C Underwood
(74) *Attorney, Agent, or Firm* — Venable LLP; Robert Kinberg (57) ABSTRACT

A method for detecting the presence of molecules includes bringing into contact with at least one optical grating comprised of a first liquid phase, a second liquid phase which cannot be mixed with the first liquid phase. The first liquid phase is arranged on a substrate in a form of periodic structures having a periodicity ranging from about 190 nm to about 10 μm. The molecules to be detected, which are capable of changing the optical characteristics of the at least one optical grating are added to the first liquid phase or to the second liquid phase either before, during or after the bringing step. The presence of molecules is detected by measuring a changed reflection or transmission of light at the at least one optical grating or a changing spatial course of the diffraction pattern as soon as the first liquid phase makes contact with the second liquid phase and with the molecules to be detected.

10 Claims, 6 Drawing Sheets

(56) References Cited

U.S. PATENT DOCUMENTS 7,118,710 B2 * 10/2006 Cunningham ............. 422/82.09
7,619,739 B1 * 11/2009 Sutherland et al. ........... 356/432

OTHER PUBLICATIONS

Lenhert, Steven et al., "Lipid Multilayer Gratings," Nature Nanotechnology, vol. 5, No. 4, pp. 275-279, Apr. 2010.
Sekula, Sylwia et al., "Multiplexed Lipid Dip-Pen Nanolithography on Subcellular Scales for the Templating of Functional Proteins and Cell Culture," Small, John Wiley and Sons, Weinheim an der Bergstrasse, vol. 4, No. 10, pp. 1785-1793, Oct. 1, 2008.
Lenhert, Steven et al., "Massively Parallel Dip-Pen Nanolithography of Heterogeneous Supported Phospholipid Multilayer Patterns," Small (Weinheim an der Berstrasse, Germany), vol. 3., No. 1, pp. 71-75, Jan. 2007.
Salaita, Khalid et al., "Applications of Dip-Pen Nanolithography," Nature Nanotechnology, Nature Publishing Group, vol. 2, No. 3, pp. 145-155, Mar. 1, 2007.
Kumar A et al., "Patterned Condensation Figures as Optical Diffraction Gratings," Science, American Association for the Advancement of Science, vol. 263, pp. 60-62, Jan. 7, 1994.

* cited by examiner

METHOD FOR DEMONSTRATING THE PRESENCE OF MOLECULES BY MEANS OF OPTICAL GRATINGS

CROSS-REFERENCE TO RELATED APPLICATIONS

This application is a U.S. National Stage of International Application No. PCT/EP2010/002534 filed Apr. 24, 2010, designating the United States and claiming priority to German application No. DE 10 2009 019 717.6 filed May 5, 2009.

BACKGROUND OF THE INVENTION

The invention relates to a method for detecting or demonstrating the presence of molecules, in particular biomolecules, which are present in a liquid phase.

The detection of molecules, especially biomolecules contained in liquids, is becoming more and more important economically, especially in the fields of biology, chemistry, biochemistry, pharmaceutics, as well as medical diagnostic and research.

The following features are critical for the practical application of a method according to the invention:
- a fast and specific detection;
- a label-free detection;
- the option of following time-dependent functions in real-time, e.g. for examining the kinetics of (bio) chemical processes;
- the suitability for using it under reactive conditions;
- the bio-compatibility; and
- the omitting of toxic components.

The following features are critical for using a device according to the invention in practical operations:
- the easy handling;
- the cost-effective implementation;
- a compact design, preferably offering the option of miniaturization up to the micrometer range, meaning along length scales in the range of or smaller than the dimensions of biological cells;
- the option of a detection inside closed (bio) chemical (reaction) vessels;
- the ability to integrate into arrays consisting of many different sensors which preferably react specifically to different substances but can be read out with the same readout mimic;
- the option of a fast, sequential and/or parallel readout of many sensors, especially via multi-channel detectors or with the aid of multiplexing;
- the option for an in-situ examination.

From a physical perspective, label-free biosensors are categorized into three groups according to the publication by Ivnitski, D; Abdel-Hamid, I.; Atanasov, P. and Wilkins, E., "*Biosensors for detection of pathogenic bacteria*," published in Biosens. Bioelectron. 14, pp 599, 1999:
1. Mass-sensitive sensors with piezoelectric materials or cantilevers for detecting the presence of biological material;
2. Electro-chemical sensors which are based on measuring the current or the resistance of a transducer; and
3. Optical sensors which substantiate the change in the refractive index or of the presence of a thin layer.

A biosensor is known from the U.S. Pat. No. 7,118,710 B2 which comprises a two-dimensional grating or grating with high refractive index, deposited on a substrate, as well as one or several specific, binding, label-free substances which are immobilized on the surface of the grating. A change in the diffraction intensity appears when illuminating the biosensor.

The International patent application Publication No. WO 2000/041213 A1 describes the dip-pen nanolithography (DPN) technique for producing structures having dimensions of 10-1000 nm by using an atomic force microscope for which the tip is wetted with a solution (ink) that is transferred by a driving force to the surface of a substrate. Owing to the humidity in the air, a watery meniscus forms between the tip and the substrate surface which functions to transfer the molecules from the tip to the surface where the molecules are absorbed chemically or where they arrange themselves on correspondingly prepared surfaces.

The European patent document EP 1881368 A2 discloses the use of membrane lipids as ink for use with the DPN, wherein the number of lipid (double) layers on the substrate surface can be adjusted via the speed of the tip on the atomic force microscope above the substrate surface and the relative humidity in the atmosphere.

The use of DPN for producing micro structures and nano structures from liquid membrane lipids which contain different shares of macro molecules and their characterization through fluorescence and photo emissions electron microscopy are described in *Multiplexed Lipid Dip-Pen Nanolithography on Subcellular Scales for the Templating of Functional Proteins and Cell Culture*, published by S. Sekula, J. Fuchs, S. Weg-Remers, P. Nagel, S. Schuppler, J. Fragala, N. Theilacker, M. Franzreb, C. Wingren, P. Ellmark, C. A. K. Borrebaeck, C. A. Mirkin, H. Fuchs and S. Lenhert, Small 4, pp 1785-1793, 2008.

In the publication Science 263, p. 60, 1994, A. Kumar and G. Whitesides describe the condensation of water on a self-organizing monolayer of ω functionalized alkane thiolates on gold. This condensation diagram forms an optical refractive grating for reflected or transmitted light with a wavelength of 632.8 nm which is subjected to an atmosphere with a constant relative humidity of the air.

SUMMARY OF THE INVENTION

Starting with this premise, it is an object of the present invention to propose a method for detecting the presence of molecules, in particular biomolecules contained in a liquid phase, without the aforementioned disadvantages and restrictions.

In particular, a method is to be made available which makes possible the fast, specific, label-free detection of low-molecular molecules as well as biomolecules.

The above and other objects are achieved according to the invention by the provision of a method for detecting the presence of molecules, which in one embodiment comprises: a) bringing into contact with at least one optical grating comprised of a first liquid phase, a second liquid phase which cannot be mixed with the first liquid phase, wherein the first liquid phase is arranged on a substrate in a form of periodic structures having a periodicity ranging from about 190 nm to about 10 µm; b) adding molecules to be detected, which are capable of changing the optical characteristics of the at least one optical grating, to the first liquid phase or the second liquid phase either before, during or after the bringing step; and c) detecting the presence of molecules by measuring a changed reflection or transmission of light at the at least one optical grating or a changing spatial course of a diffraction pattern as soon as the first liquid phase makes contact with the second liquid phase and with the molecules to be detected.

Thus, according to step (a), at least one optical diffraction grating is initially made available which consists of a first liquid phase. The liquid phase is present on a substrate in the form of periodic structures, in particular lines, points or squares, which have a periodicity of 190 nm to 10 μm. Below 190 nm, the transmission of the air is reduced in such a way that the optical detection according to step c) for all practical purposes is no longer possible while color effects cannot be observed any longer on structures with a periodicity above 10 μm.

The solid substrate may consist of glass, silicon, a polymer, preferably polymethylmethacrylate (PMMA), or a metal and in particular of gold or silver.

According to a one embodiment, the substrate surface is first functionalized, in particular through self-organizing mono-layers, a plasma treatment or precipitating out of the vapor phase. The substrate in particular may be functionalized in such a way that different regions are obtained on the surface, so that optical gratings administered to the same substrate are located on surfaces with different characteristics.

The optical grating according to another embodiment is produced with the aid of the dip-pen nanolithography (DPN). With this technique, membrane lipids, for example phospholipids may be deposited on the substrate.

Such phospholipids may include 1,2-dioleoyl-sn-glycero-3-phosphocholin, briefly DOPC, 1,2-dipalmitoyl-sn-glycero-3-phosphoethanolamine-N-(cap biotinyl), biotin lipid for short, or the nickel salt of the 1,2-di-oleoyl-sn-glycero-3-{(N (5-amino-1-arboxypentyl)iminodiacetoacidsuccinyl, abbreviated NTA lipid.

The optical grating according to an alternative embodiment is produced with the aid of a structured de-wetting of the first liquid phase on the substrate which is laterally structured or patterned with respect to its wetting characteristics. Useful in that case is the presence on the substrate of a surface roughness (grooving or roughness contrast), of chemical heterogeneities, or of geometric structures to which the first liquid phase can adhere as a result of the so-called pinning.

To produce an optical grating of this type, a liquid or a diluted solution of a liquid is applied to the substrate which is laterally structured with respect to its wetting characteristics. The grating can be produced with the aid of parallel or serial techniques, preferably stamping techniques and in particular micro-contact printing, embossing techniques, electron-beam lithography, photo lithography or laser interference lithography, as well as direct writing with the tip of a power microscope or with a laser beam. The wettable regions are subsequently covered by the liquid, thus resulting in the forming on the substrate of the periodic pattern consisting of the first liquid phase.

Additives, for example cholesterol are mixed into the first liquid phase which constitutes the at least one optical grating of special embodiments for the adjustment of the viscosity and permeability of the grating structures. Further additives are trans-membrane or peripheral membrane lipids, including natural or synthetically manufactured proteins for specific functionalities.

The at least one optical grating, made available in this way, comprises optical characteristics which can be changed by the presence of the molecular species to be detected. The optical grating characteristics for this may include:

The refractive index and the course of the refractive index as function of the location along the grating cross section;
The reflectivity of the grating;
The absorption characteristics of the grating;
The course of the intensity I ($\alpha$) as function of the angle $\alpha$;
The course of the intensity I ($\lambda$) as function of the wavelength $\lambda$ in the event of a reflection or transmission of light at the optical grating.

According to step (a), the optical diffraction grating that is made available is furthermore brought in contact with a second liquid phase which cannot be mixed with the first liquid phase. A liquid-liquid interface thus forms between the optical grating, composed of a first periodically arranged liquid phase, and the second liquid phase.

For one embodiment, the structures of the optical grating consist of a membrane lipid, and a watery solution that contains the molecules to be detected is used for the second liquid phase.

The at least one optical grating for one embodiment may be introduced into a dry gas, preferably an inert gas, prior to bringing it in contact with the second liquid phase.

According to step (b), the molecules to be detected can be ionized and added to the first liquid phase or the second liquid phase before, during, or after the optical grating with the first liquid phase is brought into contact with the second liquid phase.

According to a different embodiment, the second liquid phase already contains the molecules to be detected which have the ability to change the optical characteristics of the optical grating before the second liquid phase is brought in contact with the optical grating.

According to an alternative embodiment, the second liquid phase is initially brought in contact with the optical grating in a step (a) and the molecules to be detected, which have the ability to change the optical characteristics of the optical grating, are subsequently added to the second liquid phase.

According to yet another embodiment, the molecules to be detected are initially introduced together with the first liquid phase as a component into the optical grating, in accordance with step (a). The optical grating, which already contains the molecules to be detected, is brought only subsequently into contact with the second liquid phase.

Independent of the type and manner in which the molecules to be detected are introduced, the detection of the molecules occurs only if the molecules to be detected come in contact with the second liquid phase as well as directly with the first liquid phase of the optical grating.

The special capability of the molecules to be detected to change the optical characteristics of the optical grating is a precondition for making possible the detection of the molecular species during step (c) via a change in the intensity or the spatial course of the diffraction pattern.

In particular molecules capable of changing the geometric form, the optical density and/or the absorption characteristics of the optical grating are suitable for realizing the method according to the invention.

According to one embodiment, molecules are used which change the interface energy of the optical grating below a surrounding liquid, thus advantageously causing a de-wetting processes on the substrate.

According to a different embodiment, molecules are used which change the form of the grating, and thus its optical characteristics, by changing the wetting angle of the grating lines, relative to the substrate.

According to yet another embodiment, molecules are used which form an intercalation product with the first liquid phase of the grating and, in this way, change the optical characteristics of the grating.

The molecules used according to a different embodiment form a chemical compound through reaction with the liquid phase of the grating, wherein the presence of this compound changes the optical characteristics of the grating. Organic molecules, especially vapors containing alcoholic agents or substances with higher volatility, tensides, or biomolecules and especially proteins and nucleic acids are preferably used for this.

The changes in the characteristics of the at least one optical diffraction grating, caused by the molecules to be detected, are finally detected during step (c). The changes are detected via a change in the intensity and/or a change in the diffraction pattern which follows from the reflection or the transmission of light, preferably arriving from a laser or another coherent light source, at the optical grating.

The detection of the molecules is based on the idea of detecting a number N of information bits, meaning the concentrations N of the various molecules, by detecting at least N parameters with the aid of measurements and by knowing the dependence of each of these parameters as function of the concentration of each of the molecules to be detected. The knowledge of these parameters as function of the concentration of each of the molecules to be detected in this case is preferably obtained through calibration measurements, wherein respectively only one molecule species is present in the analyte and all N parameters are measured as a function of the concentration of these species.

For the non-specific detection, we proceed on the assumption that the molecules to be detected are known and that only the concentration or presence of these molecules, meaning proof of the concentration above a detection limit, must be determined. In that case, several molecular species can also be detected simultaneously, without the option of distinguishing between them.

The concentration of the molecules to be detected in the second liquid phase preferably functions as a measure for the change in the optical characteristics of the optical grating. In this way, it is not only possible to detect the searched-for molecular species, but also to analyze its concentration and the dependence of this concentration on the time via the observation interval.

For the specific detection, the method according to the invention advantageously uses of the following embodiments.

According to a first embodiment, the concept of the specific bond is used, especially based on the biochemical lock-and-key principle and/or the fit-induced fit principle. For this, additional molecules are introduced into the at least one optical grating or into the second liquid phase, wherein these molecules enter into a specific bond with the molecules to be detected, so that the optical characteristics of the optical grating in the process change in such a way that the specific bond permits a detection of the molecules to be detected.

According to an alternative embodiment, a plurality of optical gratings is used for the detection, wherein the individual optical gratings differ in at least one characteristic (so-called chemical fingerprint). Particularly suitable for this are the first liquid phase which is used for the grating, the selected second liquid phase, the additives in the first liquid phase used for the grating, the additives in the selected second liquid phase and/or the material, the coating, the coating pattern or the degree of roughness of the substrate.

At least two optical gratings are in particular provided for this, wherein these gratings differ with respect to the height of the periodic structures.

As a result, the reaction of the optical grating to the molecule to be detected can be controlled via the grating height.

The concept of the so-called physical fingerprint is used according to another embodiment. For this, the same grating is read out under different angles and/or at different wavelengths. Alternatively, an additional physical characteristic, especially the refractive index, is read out for different parameter values of a physical variable. It is advantageous in that case that only a single optical grating is needed.

In particular, a plurality of optical gratings is admitted with light from the same light source (laser) and the values read out with the same detector system. Suitable for use are multi-channel detector systems, e.g. a CCD chip (parallel readout) and/or laser scanning and/or multiplexing (sequential readout).

The method according to the invention proposes a fast, easy to handle, cost-effective detection method which can be realized without special knowledge and which provides the options of a specific detection as well as a biomolecular detection. Numerous channels can be read out in parallel or sequentially with the aid of a simple, optical readout technique, using commercially available and miniaturized scanners, thereby allowing a miniaturization all the way down to the micrometer scale and thus the length scale used for biological cells.

The specificity of the detection is permitted by the option of using standard methods for the biomolecular detection, thereby making it possible to detect the resulting changes in the diffraction characteristics of the liquid grating easily, quickly and time-resolved as well as with high sensitivity.

The optical detection furthermore makes it possible to use optically transparent walls, e.g. made of glass or PMMA, for carrying out real-time analyses of the concentration inside closed containers and to provide a specific detection of molecular species. As a result, numerous parallel-operating scanners can be used inside a closed container which can be read out contactless with the aid of scanners located on the outside (remote reading).

BRIEF DESCRIPTION OF THE DRAWINGS

The invention is explained in further detail in the following with the aid of several exemplary embodiments shown in FIGS. 1-8.

DETAILED DESCRIPTION

Optical gratings composed of lyotropic liquid crystals with a period of 500-800 nm are used for the exemplary embodiments shown in FIGS. 1-5, wherein the gratings consist of regular structures of the phospholipid 1,2-dioleoyl-sn-glycero-3-phosphocholin (DOPC), applied with the aid of dip pen nanolithography (DPN) to the surfaces of polymethylmethacrylate (PMMA), previously treated for respectively 5 minutes with ultrasound while subjected to isopropanol and ultra-clean water.

For detecting the presence of the molecules brought in contact with the grating, the grating was subjected to white light transmitted at an angle of approximately 70°, relative to the surface. The light which was diffracted normally, relative to the surface, was recorded with the aid of a color CCD camera.

Figure 1:
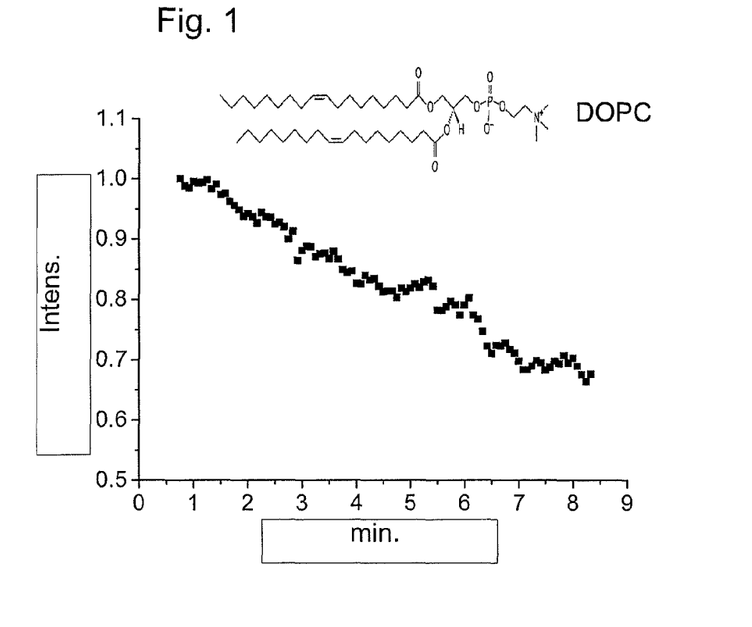

FIG. 1 shows a comparison measurement in which the intensity of the light, diffracted by an optical grating of this type, located in the air, is plotted in random units relative to the time, wherein the molecules to be detected were not plotted thereon. Based on the humidity in the air, the observed intensity decreases monotonously over time.

In FIGS. 2-5, the intensity of the diffracted light is respectively plotted in random units, relative to the time. The arrows in each case denote the point in time when the grating was subjected to vapors and/or solutions containing the respectively labeled molecules.

Figure 2:
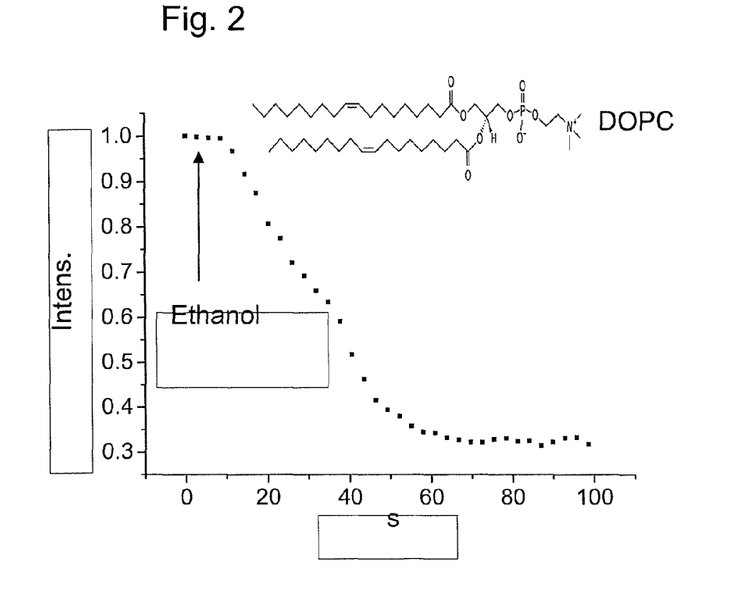

In FIG. 2, ethanol vapors were added at point in time 0 s.

Figure 3:
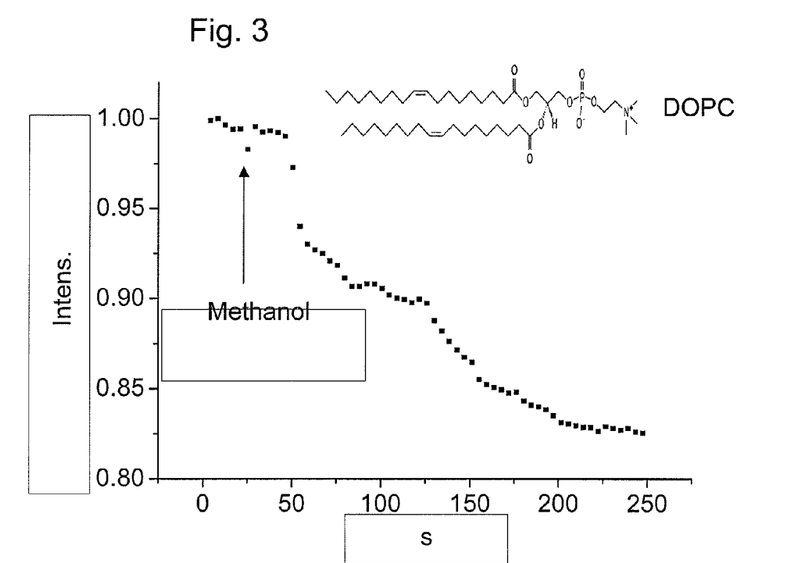

In FIG. 3, methanol vapors were added at point in time 25 s.

Figure 4:
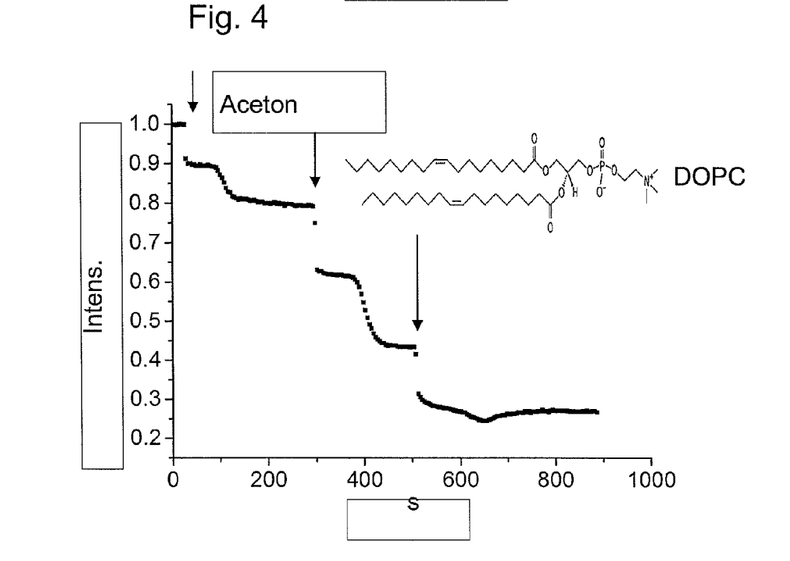

In FIG. 4, acetone vapors were respectively added at points in time 0 s, 250 s and 500 s.

Figure 5:
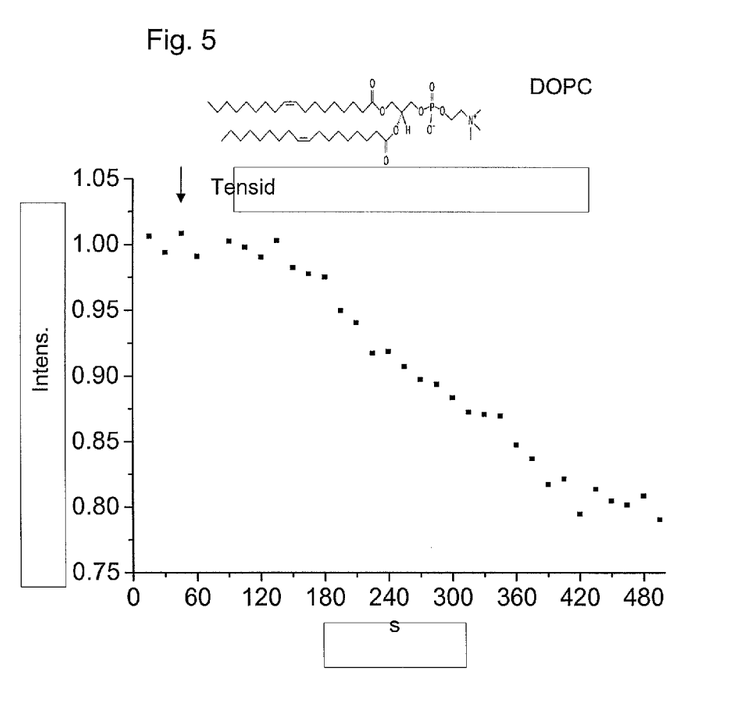

In FIG. 5, a 5 nM solution of the tenside Triton-X 100 was added at point in time 50 s, wherein the grating was submerged for at least 5 minutes into pure water under a nitrogen atmosphere prior to the admixture of the tenside. The intensity of the diffracted light did not change substantially during this time interval.

Figure 6:
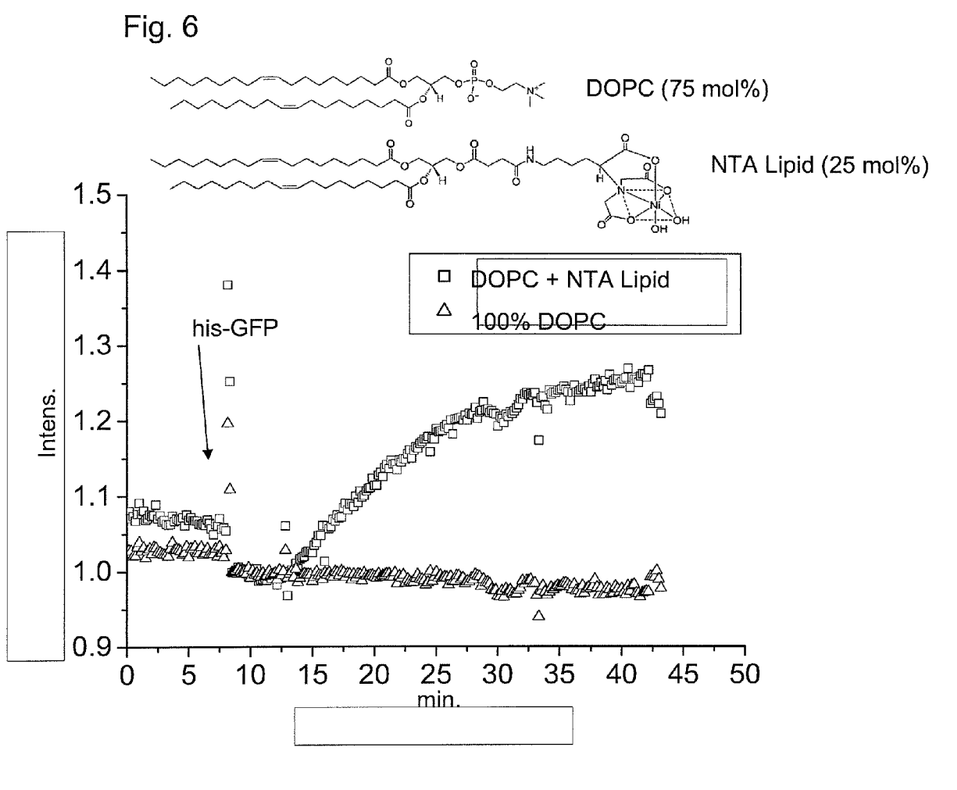

With the experiment shown in FIG. 6, a 50 nM solution of the protein polyhistidine tagged green fluorescent protein, abbreviated his-GFP, was brought into contact with the grating at the point in time that is marked by an arrow. However, only the red share of the diffracted light was used for the detection since the protein his-GFP emits in the green spectral range and the intent was to preclude an interference with the green share of the intensity of the diffracted light.

The optical grating was produced as shown in FIGS. 1-4. However, a mixture of 75% DOPC and 25% NTA lipid, the pattern of which is shown in FIG. 6, was used as material for the optical grating according to FIG. 6. In addition and to serve as a comparison, an optical grating of pure DOPC was produced on the same surface in order to demonstrate the specificity of the detection. Once they were produced, the optical gratings were dipped into a solution of phosphate-buffered silane which contained 0.5 weight % BSA (bovine serum albumin) to prevent a non-specific bond. In FIG. 6, the intensities of the diffracted light are respectively shown in random units with squares for the optical grating, consisting of the mixture, and triangles for the optical grating consisting of the pure DOPC.

Figure 7:
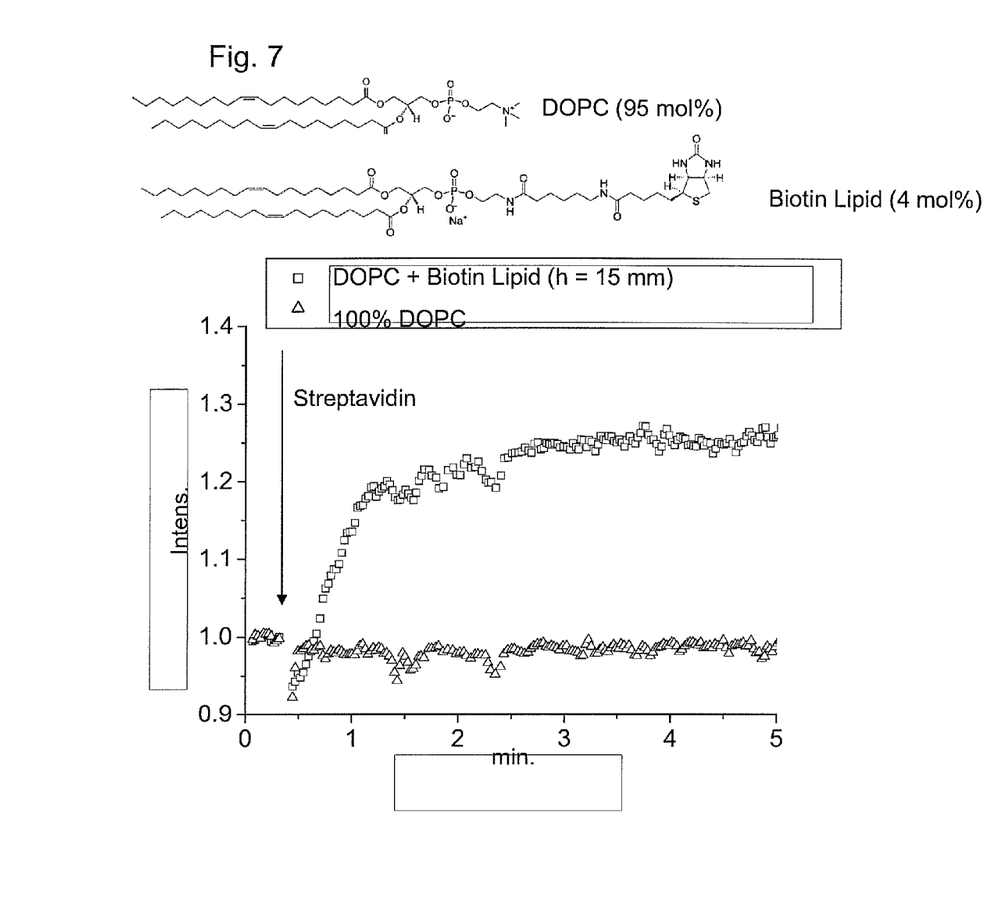
Figure 8:
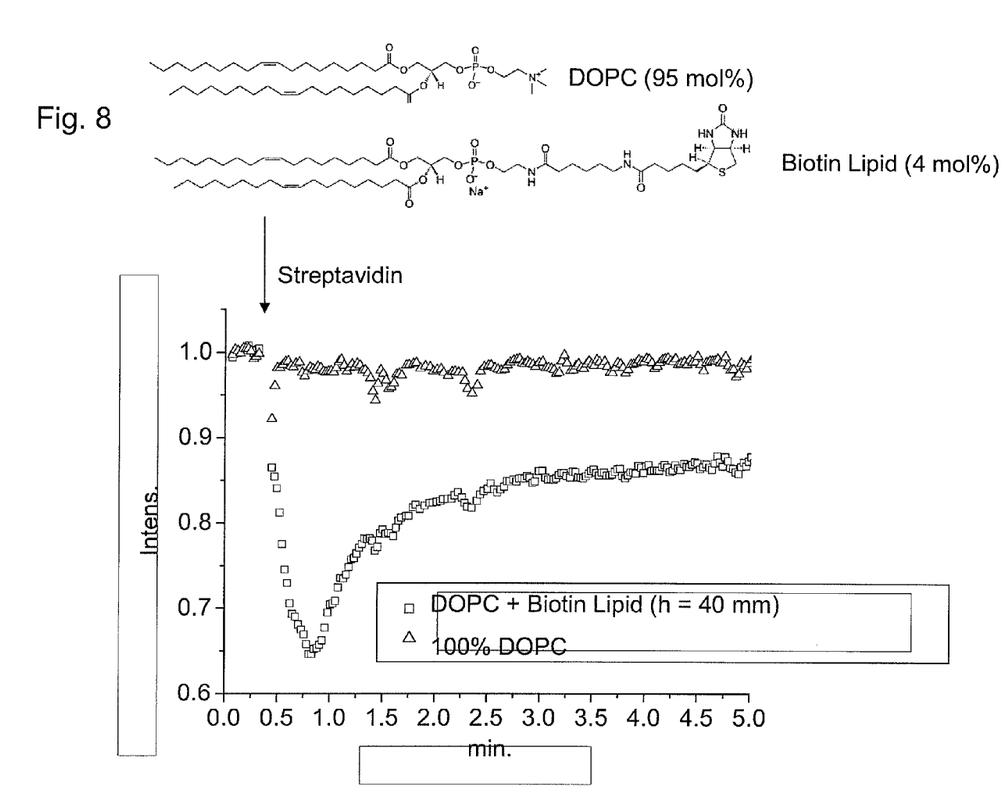

In FIGS. 7 and 8, a 50 nM solution of the protein streptavidin was brought in contact with the grating, respectively at the point in time marked with an arrow. The optical grating was produced as shown in FIGS. 1-4. However, for the grating shown in FIGS. 7 and 8, a mixture of 95% DOPC and 5% biotinylated lipid, abbreviated biotin lipid having a structure as shown in FIGS. 7 and 8, was used as material for the optical grating. For the comparison, an optical grating of pure DOPC was again produced on the same surface to demonstrate the specificity of the detection. Following their completion, the optical gratings in question were again dipped into a solution of phosphate-buffered silane which contained 0.5 weight % BSA to prevent a non-specific bond.

FIGS. 7 and 8 respectively show the intensities of the diffracted light in random units with squares for the optical grating consisting of the mixture and with triangles for the optical grating consisting of pure DOPC.

The difference between FIGS. 7 and 8 is that in FIG. 7 the height of the optical grating was approximately 15 nm and in FIG. 8 it was approximately 40 nm. The clearly different course of the diffraction intensities over time demonstrates that the height of the grating structures can be used for adjusting the reaction of the optical grating to the molecule to be detected. In FIG. 7, the optical grating primarily reacts to the intercalation of the analyte while in FIG. 8, the decrease in the intensity could be traced back to the de-wetting of the grating elements from the substrate, based on the presence of the analyte.

The invention claimed is:

1. A method for detecting the presence of molecules, comprising:
   a) bringing into contact with at least one optical grating comprised of a first liquid phase, a second liquid phase which cannot be mixed with the first liquid phase, wherein the first liquid phase is arranged on a substrate in a form of periodic structures having a periodicity ranging from about 190 nm to about 10 µm;
   b) adding molecules to be detected, which are capable of changing the optical characteristics of the at least one optical grating, to the first liquid phase or the second liquid phase either before, during or after the bringing step; and
   c) detecting the presence of molecules by measuring a changed reflection or transmission of light at the at least one optical grating or a changing spatial course of the diffraction pattern as soon as the first liquid phase makes contact with the second liquid phase and with the molecules to be detected.

2. The method according to claim 1, including producing the at least one optical grating with the aid of dip-pen nano-lithography, micro-pipettes, micro-contact pressure, through structured de-wetting of the first liquid phase on the substrate or through melting of a lithographically structured solid material.

3. The method according to claim 1, including producing the at least one optical grating by depositing the first liquid phase on a substrate having a surface roughness, topographies, chemical heterogeneities or geometric structuring to which the structures of the first liquid phase can adhere.

4. The method according to claim 1, including producing the optical grating with structures comprising a membrane lipid; and wherein the adding step includes using a watery solution with therein contained molecules to be detected for the second liquid phase.

5. The method according to claim 1, including producing the optical grating by introducing additional molecules into the first liquid phase, of which the optical grating is composed, wherein said additional molecules enter into a bond with the molecules to be detected, such that the characteristics of the optical grating are changed in the process.

6. The method according to claim 1, wherein the detecting step includes reading out at least one optical grating under different angles or at different wavelengths.

7. The method according to claim 1, including using at least two optical gratings which differ in their optical characteristics.

8. The method according to claim 7, wherein the using step includes using at least two optical gratings for which the height of the periodic structures is different.

9. The method according to claim 1, wherein the molecules detected by the detecting step comprise organic molecules or biomolecules.

10. The method according to claim 1, wherein the molecules detected by the detecting step comprise tensides, proteins or nucleic acids.

* * * * *